United States Patent
Di Leo

(10) Patent No.: US 9,086,178 B2
(45) Date of Patent: Jul. 21, 2015

(54) PUMP HOSE FOR A PERISTALTIC PUMP

(71) Applicant: Connectors Verbindungstechnik AG, Tagelswangen (CH)

(72) Inventor: Vito Di Leo, Kloten (CH)

(73) Assignee: Connectors Verbindungstechnik AG, Tagelswangen (CH)

( * ) Notice: Subject to any disclaimer, the term of this patent is extended or adjusted under 35 U.S.C. 154(b) by 0 days.

(21) Appl. No.: 14/357,321

(22) PCT Filed: Oct. 16, 2012

(86) PCT No.: PCT/EP2012/070466
§ 371 (c)(1),
(2) Date: May 9, 2014

(87) PCT Pub. No.: WO2013/068206
PCT Pub. Date: May 16, 2013

(65) Prior Publication Data
US 2014/0318660 A1    Oct. 30, 2014

(30) Foreign Application Priority Data
Nov. 11, 2011   (EP) ..................... 11188816

(51) Int. Cl.
*F16L 11/00*   (2006.01)
*F16L 33/00*   (2006.01)
*F04B 43/00*   (2006.01)
(Continued)

(52) U.S. Cl.
CPC ............. *F16L 33/00* (2013.01); *F04B 43/0072* (2013.01); *F04B 43/06* (2013.01); *F04B 43/08* (2013.01); *F04B 43/12* (2013.01); *F04B 45/06* (2013.01); *F04B 45/08* (2013.01); *F16L 33/28* (2013.01); *A61M 39/10* (2013.01)

(58) Field of Classification Search
USPC .................................. 138/109, 119, DIG. 11
See application file for complete search history.

(56) References Cited

U.S. PATENT DOCUMENTS 3,582,234 A * 6/1971 Isreeli et al. ..................... 417/53
4,653,542 A * 3/1987 Tascher ......................... 138/109
(Continued)

FOREIGN PATENT DOCUMENTS

DE        92 08 212 U1    10/1992
DE        101 31 563 A1    1/2002
(Continued)

*Primary Examiner* — James Hook
(74) *Attorney, Agent, or Firm* — George Pappas

(57) ABSTRACT

In order to improve a pump hose that is suitable for a peristaltic pump whereby transitions within the hose are avoided and which furthermore is operationally reliable, there is suggested a pump hose having a tubular center part (11) to which are arranged at both sides thereof connecting parts (12, 14) for connecting the pump hose (10) to other elements and having flange parts (17, 18) arranged at both sides for insertion into a cartridge part of the peristaltic pump. The tubular center part (11), the connecting parts (12, 14) arranged at both sides thereof and the flange parts (17, 18) arranged at both sides thereof are integrally produced from silicone. The connecting parts (12, 14) each have a head-like shaped sealing surface (16). The sealing surface (16) is surrounded by a substantially circular sealing bulge (20) that protrudes longitudinally beyond the sealing surface (16). The flange parts (17, 18) comprise nubs (22) whereby the pump hose (10) is inserted in a non-gas-tight manner, preferably also in a non-fluid-tight manner, into the peristaltic pump segment.

13 Claims, 1 Drawing Sheet

(51) Int. Cl.
*F04B 43/06* (2006.01)
*F04B 43/08* (2006.01)
*F04B 43/12* (2006.01)
*F04B 45/06* (2006.01)
*F04B 45/08* (2006.01)
*F16L 33/28* (2006.01)
*A61M 39/10* (2006.01)

(56) References Cited

U.S. PATENT DOCUMENTS

| | | | |
|---|---|---|---|
| 5,088,522 A | 2/1992 | Rath et al. | |
| 5,213,483 A | 5/1993 | Flaherty et al. | |
| 5,215,450 A * | 6/1993 | Tamari | 417/474 |
| 5,242,279 A | 9/1993 | Knuth | |
| 5,388,972 A | 2/1995 | Calhoun et al. | |
| 6,494,692 B1 | 12/2002 | Green | |
| 2002/0001530 A1 | 1/2002 | Doi et al. | |
| 2006/0083644 A1 * | 4/2006 | Zumbrum et al. | 417/476 |
| 2008/0178957 A1 * | 7/2008 | Thomas et al. | 138/121 |
| 2008/0248226 A1 * | 10/2008 | Simon et al. | 428/34.9 |
| 2011/0315122 A1 * | 12/2011 | Straub | 123/469 |

FOREIGN PATENT DOCUMENTS

| | | |
|---|---|---|
| DE | 10 2004 024641 A1 | 12/2005 |
| EP | 0 388 596 A1 | 9/1990 |
| EP | 0 526 920 A1 | 2/1993 |
| EP | 1 048 848 A1 | 2/2000 |

* cited by examiner

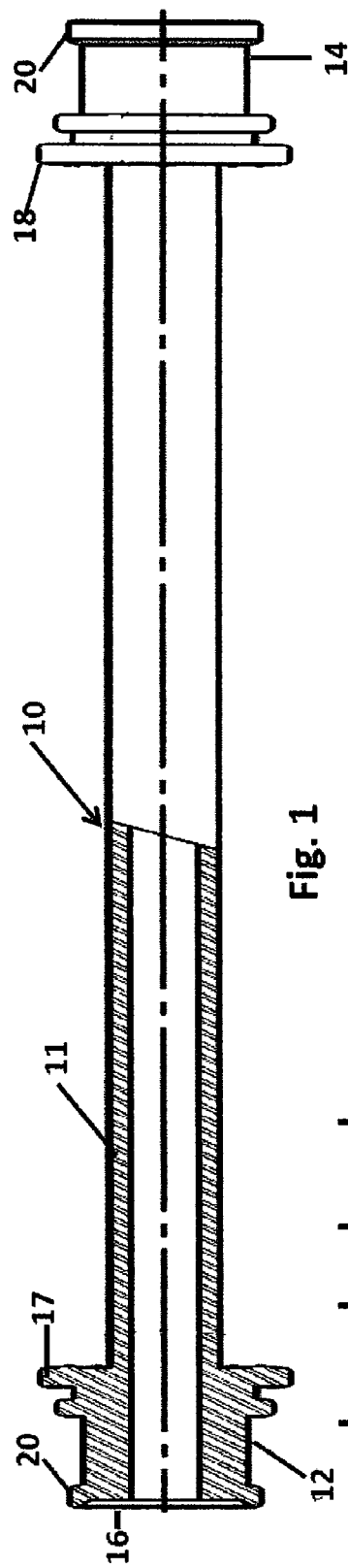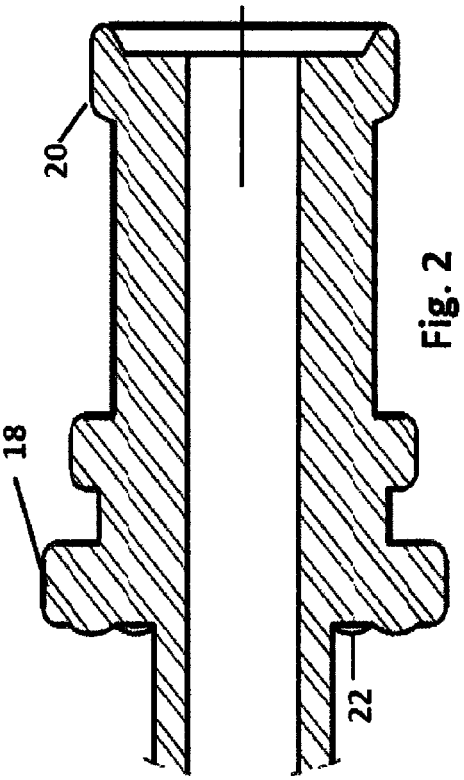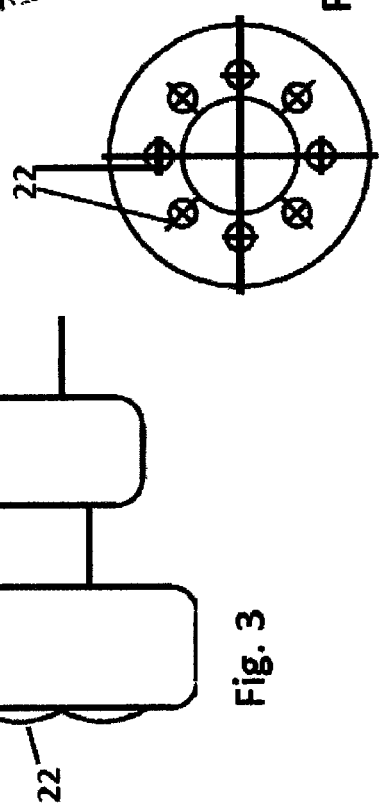

PUMP HOSE FOR A PERISTALTIC PUMP

This application claims priority from PCT application No. PCT/EP2012/070466 filed Oct. 16, 2012 which claims priory from European application No. EP 11188816.0 filed on Nov. 11, 2011, the disclosures of which are incorporated herein by reference.

FIELD OF THE INVENTION

The invention relates to a pump hose, in particular to a silicone pump hose, for a peristaltic pump.

BACKGROUND OF THE INVENTION

Peristaltic pumps are used to produce a forward movement of a liquid by means of a squeezing process. Such peristaltic pumps comprise a pump segment into which the hose is usually inserted. The pump segment is then provided with a driving device for the peristaltic squeezing process. The pump hose usually comprises connecting devices that are intended for the elements for supplying the pump with the liquid and for the recipient. The advantage of such a peristaltic pump is that substantial parts of the pump segment, particularly the driving segment, do not come into contact with the liquid to be pumped peristaltically. This is particularly advantageous in the field of biotechnology, where the liquid to be pumped should be sterile. But also in the case of contaminated liquids in the field of biotechnology or in the technology of radioactively contaminated liquids such a peristaltic pump is advantageous.

Thereby the pump hose is usually configured as a disposable part that is usually supplied in sterile condition and that does not need to be used anymore after a possible contamination.

From U.S. Pat. No. 5,213,483 A there is known a peristaltic pump with a pump head housing of the above mentioned type. From U.S. Pat. No. 5,388,972 A there is known a precision pump head.

From EP 0 388 596 A1 there is known a silicone pump hose for a peristaltic pump for insertion into a peristaltic pump segment with a tubular center part and connecting parts arranged at both sides thereof for insertion or connection of the pump hose. The sealing front faces slightly protrude into the hose. At one of the front faces the hose is surrounded in the region of its connecting parts by a substantially circular sealing bulge. From DE 101 31 563 A1 there is known a hose with identical connecting parts at the two sides thereof.

In EP 1 048 848 A1 there is suggested a peristaltic pump head wherein the flange is fitted in fluid-tight manner into a recess. However, this has not been found to be advantageous in every case because thereby certain strains of the peristaltic pump can occur, which should be avoided.

On the other hand, the construction of EP 1 048 848 A1 has turned out to be very disadvantageous. Therein it is suggested that a terminal fitting, that is, a connecting part, is injection-molded onto the pump hose or attached thereto. However, this means that transitions—within the hose—cannot be avoided. However, as a part of the object of the present invention, transitions should at least be avoidable.

SUMMARY OF THE INVENTION

An object of the present invention is to propose a pump hose that is improved in respect to the prior art and is suitable for a peristaltic pump, and by means of which transitions within the hose may be avoided. Hereby, the measures of the invention have firstly the result that no injection molding or attaching of a connecting part (fitting) is necessary and that thus the above described problems are avoided. The embodiment of the pump hose from silicone, preferably from platinum-linked silicone, results in an increase of the quality. Due to the fact that the connecting parts each have a head-like shaped sealing surface and that the sealing surface is surrounded by a substantially circular sealing bulge that protrudes longitudinally beyond the sealing surface, the connecting parts can be attached in a direct and particularly advantageous manner to the elements for supplying the pump with the liquid and to the recipient. To avoid pressure fluctuations etc. it is advantageous if the flange parts comprise means for inserting the pump hose in a non-gas-tight manner, preferably also in a non-fluid-tight manner, into the peristaltic pump segment. Such means can comprise nubs that are formed towards the tubular center part, which ensure a small slippage.

It is advantageous if the inside of the pump hose is configured transitionless between the two sealing surfaces. Of course, this is not necessary. It would also be possible to provide certain transitions if this is desired in exceptional situations.

In order to achieve a facilitated flange-mounting, it is advantageous if the flange parts (17, 18) have a distance from the sealing bulge (20), for example a distance of about 35 mm.

To facilitate the connection to the elements for supplying the pump with the liquid and to the recipient, the pump hose is preferably provided with a retaining ring that at least partially projects over the sealing bulge and is preferably made of a hard plastic. This retaining ring made of a hard material can then press the sealing bulge and concomitantly the sealing surface forward or backward against the corresponding counterface of the elements for supplying the pump with the liquid and of the recipient without a need for exerting a direct force influence onto the soft silicone hose.

The aforementioned elements as well as those claimed and described in the following exemplary embodiments, to be used according to the invention, are not subject to any particular conditions by way of exclusion in terms of their size, shape, use of material and technical design, with the result that the selection criteria known in the respective field of application can be used without restrictions.

BRIEF DESCRIPTION OF THE DRAWINGS

Examples of the invention will henceforth be described in more detail by reference to the drawings, which show:

FIG. 1 a side view of a pump hose of the present invention,
FIG. 2 a detail view of one of the flange parts with the connecting part according to FIG. 1, from the side;
FIG. 3 a detail view of FIG. 2 with the flange part with the nubs, from the side; and
FIG. 4 a view onto the flange part of the pump hose seen from the center part with the distance nubs.

DESCRIPTION OF THE PREFERRED EMBODIMENTS

A preferred exemplary embodiment, as shown in FIG. 1, shows a pump hose 10, namely a silicone pump hose for a peristaltic pump. The pump hose 10 consists principally of five partial portions, namely a tubular center part 11, connecting parts 12 and 14 arranged at both sides thereof, for connecting the pump hose 10 to other elements, namely to the elements for supplying the pump with the liquid and to the recipient of the pumped liquid, which are not shown, and flange parts 17 and 18, arranged at both sides thereof, for insertion into a cartridge part of the peristaltic pump.

All the five partial portions of the silicone pump hose, namely the tubular center part 11, the connecting parts 12 and 14 arranged at both sides thereof, and the flange parts 17 and 18 arranged at both sides thereof between the center part and the connecting parts, are integrally produced from silicone, in the present exemplary embodiment from platinum-linked silicone. Due to this fact, the silicone pump hose can be sterilized in a particularly convenient manner, in particular by flame sterilization, whereby it is avoided that, for example, connecting parts (fittings) that are injection-molded or otherwise attached thereto, could be detached or otherwise be damaged. Moreover, transitions can be avoided by the integral formation. Moreover, by virtue of the integral forming method it is possible, as in the present exemplary embodiment, to provide each of the connecting parts 12 and 14 with a head-like shaped sealing surface 16. Because the sealing surfaces 16 are a part of the integrally formed hose, it is possible to avoid sealing rings, which have been found to be contamination-prone before and after use in the hoses according to prior art. In the exemplary embodiment the sealing surfaces 16 are surrounded by a substantially circular sealing bulge 20 that protrudes longitudinally beyond the sealing surface 16.

In the exemplary embodiment the sealing bulge 20 is chamfered towards the sealing surface, that is in inward direction, by about 70°.

In the exemplary embodiment the flange parts 17 and 18 are located about 35 mm away from the sealing surface, measured at the surfaces facing away from the sealing surface. These surfaces of the flange parts 17 and 18, which are facing away from the sealing surface, comprise, in the present exemplary embodiment, means for inserting the pump hose (10) into the peristaltic pump segment in a non-gas-tight manner, preferably also in a non-fluid-tight manner. In this manner potentially occurring tensions arising from movements resulting from the elasticity of the material, that is silicone, and hence from the flexible length thereof, particularly during the peristaltic movements, are avoided or reduced. In the present exemplary embodiment these means are formed as nubs 22, namely as eight nubs distributed about the circumference with an elevation of about 0.5 to 1 mm.

In the present exemplary embodiment, there is provided a retaining ring (not shown here), which is made of a hard plastic and at least partially projects over the sealing bulge (20), for attaching the pump hose 10 to the other elements of the peristaltic pump. The retaining ring is slidingly arranged between the flange part 17 or 18 and the respective sealing bulge 20. By virtue of this retaining ring, any forces that occur upon connection and may potentially damage the silicone material can be avoided because these forces are absorbed by the retaining ring.

LIST OF REFERENCE NUMERALS

10 pump hose
11 center part
12 connecting part
14 connecting part
16 sealing surface
17 flange part
18 flange part
20 sealing bulge
21 the inside of the pump hose
22 nubs

The invention claimed is:

1. A silicone pump hose, for a peristaltic pump, for insertion into a peristaltic pump segment, comprising
   a tubular center part,
   connecting parts arranged at both sides thereof, for connecting the pump hose to other elements,
   flange parts arranged at both sides thereof for insertion into a cartridge part of the peristaltic pump,
   characterized in that
   the tubular center part, the connecting parts arranged at both sides thereof and the flange parts arranged at both sides thereof are integrally produced from silicone,
   the connecting parts each have a head-like shaped sealing surface,
   wherein the sealing surface is surrounded by a substantially circular sealing bulge that protrudes longitudinally beyond the sealing surface, and
   wherein the flange parts comprise means for inserting the pump hose in a non-gas-tight manner into the peristaltic pump segment, and the said means comprise nubs that are formed towards the tubular center part.

2. Pump hose according to claim 1, characterized in that the inside of the pump hose is configured transitionless between the two sealing surfaces.

3. Pump hose according to claim 2, characterized in that the flange parts have a distance from the sealing surface.

4. Pump hose according to claim 2, characterized by a retaining ring that at least partially projects over the sealing bulge for attaching the pump hose to the other elements of the peristaltic pump, the inside of the pump hose being configured transitionless between the two sealing surfaces, the retaining ring being slidingly arranged between the flange part and the sealing bulge.

5. Pump hose according to claim 4, wherein the retaining ring is made of hard plastic.

6. Pump hose according to claim 1, characterized in that the flange parts have a distance from the sealing surface.

7. Pump hose according to claim 6, characterized in that the distance is about 35 mm.

8. Pump hose according to claim 6, characterized by a retaining ring that at least partially projects over the sealing bulge for attaching the pump hose to the other elements of the peristaltic pump, the inside of the pump hose being configured transitionless between the two sealing surfaces, the retaining ring being slidingly arranged between the flange part and the sealing bulge.

9. Pump hose according to claim 8, wherein the retaining ring is made of hard plastic.

10. Pump hose according to claim 1, characterized by a retaining ring that at least partially projects over the sealing bulge for attaching the pump hose to the other elements of the peristaltic pump, the inside of the pump hose being configured transitionless between the two sealing surfaces, the retaining ring being slidingly arranged between the flange part and the sealing bulge.

11. Pump hose according to claim 10, wherein the retaining ring is made of hard plastic.

12. Pump hose according to claim 1, wherein the tubular center part, the connecting parts arranged at both sides thereof and the flange parts arranged at both sides thereof are integrally produced from platinum-linked silicone.

13. Pump hose according to claim 1, wherein the pump hose is inserted into the peristaltic pump segment also in a non-fluid-tight manner.

* * * * *